United States Patent
Yogi et al.

(10) Patent No.: US 9,664,678 B2
(45) Date of Patent: May 30, 2017

(54) AUTOMATED ANALYZER AND ANALYZING METHOD

(75) Inventors: Takeshi Yogi, Tokyo (JP); Sakuichiro Adachi, Tokyo (JP); Tomonori Mimura, Tokyo (JP); Hajime Yamazaki, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 75 days.

(21) Appl. No.: 14/238,060

(22) PCT Filed: Sep. 3, 2012

(86) PCT No.: PCT/JP2012/072291
§ 371 (c)(1),
(2), (4) Date: Mar. 24, 2014

(87) PCT Pub. No.: WO2013/042524
PCT Pub. Date: Mar. 27, 2013

(65) Prior Publication Data
US 2014/0220705 A1    Aug. 7, 2014

(30) Foreign Application Priority Data

Sep. 20, 2011  (JP) .................................. 2011-204916

(51) Int. Cl.
*G01N 21/51* (2006.01)
*G01N 33/543* (2006.01)
(Continued)

(52) U.S. Cl.
CPC ....... *G01N 33/54366* (2013.01); *G01N 21/51* (2013.01); *G01N 21/82* (2013.01);
(Continued)

(58) Field of Classification Search
None
See application file for complete search history.

(56) References Cited

U.S. PATENT DOCUMENTS

| 4,451,433 A | 5/1984 | Yamashita et al. |
|---|---|---|
| 5,123,731 A | 6/1992 | Yoshinaga et al. |

(Continued)

FOREIGN PATENT DOCUMENTS

| JP | 54-108694 A | 8/1979 |
|---|---|---|
| JP | 55-159157 A | 12/1980 |

(Continued)

OTHER PUBLICATIONS

Extended European Search Report received in European Application No. 12834164.1 dated Mar. 20, 2015.

(Continued)

*Primary Examiner* — Rebecca Martinez
(74) *Attorney, Agent, or Firm* — Mattingly & Malur, PC (57) ABSTRACT

An analyzer provides conditions suitable for a reagent for performing latex immunoassay with a high sensitivity using a method of measuring scattered light. Irradiation light having a wavelength in the range of 0.65 to 0.75 μm is used, and scattered light generated from a reaction solution is received at a light-receiving angle of 15° to 35° with respect to the irradiation direction during the rotational movement of the reaction container. The reagent contains latex particles the average peak particle diameter of which ranges from 0.3 μm to 0.43 μm and to which antibodies are sensitized. The reaction solution contains latex particles at a concentration at which the absorbance to irradiation light having a wavelength of 0.7 μm is 0.25 abs to 1.10 abs, and a change in the amount of scattered light caused by the aggregation of the latex particles through antigens in a sample is measured and quantified.

8 Claims, 4 Drawing Sheets

(51) Int. Cl.
 *G01N 21/82* (2006.01)
 *G01N 35/02* (2006.01)
 *G01N 21/47* (2006.01)
 *G01N 35/04* (2006.01)

(52) U.S. Cl.
 CPC ..... *G01N 33/54313* (2013.01); *G01N 35/025* (2013.01); *G01N 21/47* (2013.01); *G01N 2021/825* (2013.01); *G01N 2035/0441* (2013.01); *G01N 2035/0443* (2013.01); *G01N 2035/0444* (2013.01); *G01N 2800/24* (2013.01)

(56) References Cited

U.S. PATENT DOCUMENTS

| | | |
|---|---|---|
| 6,791,676 B1 | 9/2004 | Meller |
| 8,852,511 B2 * | 10/2014 | Adachi ................. G01N 21/51 422/50 |
| 2010/0221741 A1 * | 9/2010 | Saiki .................... G01N 33/491 435/7.1 |

FOREIGN PATENT DOCUMENTS

| | | |
|---|---|---|
| JP | 2000-275245 A | 10/2000 |
| JP | 2001-074742 A | 3/2001 |
| JP | 2001-141654 A | 5/2001 |
| JP | 2001-228154 A | 8/2001 |
| JP | 2001-330615 A | 11/2001 |
| JP | 2011-174842 A | 9/2011 |
| WO | 2011/004781 A1 | 1/2011 |
| WO | WO2011/004781 * | 1/2011 |

OTHER PUBLICATIONS

Bohren et al., "Absorption and Scattering of Light by Small Particles", J. Wiley & Sons, 1983.

* cited by examiner

AUTOMATED ANALYZER AND ANALYZING METHOD

TECHNICAL FIELD

The present invention relates to a method and an analyzer that measure the aggregation reaction of small particles using an antigen-antibody reaction by light scattering, and more particularly, to a method of measuring scattered light on an automated analyzer.

BACKGROUND ART

Automated analyzers are widely used, which irradiate a reaction solution into which a sample and a reagent are mixed with light from a light source, calculate absorbance from a change in the amount of transmitted light of a specific wavelength, and quantify the concentration of a substance to be measured in a blood sample according to the Lambert-Beer law (see PTL 1, for example). These automated analyzers are provided with multiple cells holding the reaction solution on the circumference of a cell disc that repeats rotation and stop, obtain time-series data of the amount of light transmitted through the reaction solution in the cell as reaction process data for about 10 minutes at intervals of about 15 seconds in a transmitted light measuring unit disposed at a predetermined position during rotation of the cell disc, calculate absorbance from a change in the amount of the light, and qualify the concentration of a substance to be measured.

An automated analyzer mainly measures two types of reactions: a color reaction between a substrate and an enzyme and an immune reaction between an antigen and an antibody. Analysis using the former reaction is referred to as a biochemical analysis, and its test items are lactate dehydrogenase (LDH), alkaline phosphatase (ALP), aspartate aminotransferase (AST), and the like. Analysis using the latter reaction is referred to as immunoassay, and its test items are C-reactive protein (CRP), immunoglobulin (IgG), rheumatoid factor (RF), and the like. Test items that are required for quantification in the low range of blood concentration are present in some substances measured by the latter. For such test items, latex immunoassay is performed that uses latex particles on the surface of which antibodies are sensitized (bound) as a sensitizer (see PTL 2, for example).

In the latex immunoassay, the antibody on the surface of latex particles contained in a reagent recognizes and binds the antigen as a substance to be measured contained in a sample, and as a result the latex particles aggregate through the antigen and the aggregate of latex particles are produced. A conventional automated analyzer irradiates a reaction solution into which aggregates are dispersed with light, and measures the amount of transmitted light that passes through without being scattered by the aggregates of the latex particles. The higher the concentration of the antigen, the size of the aggregate after a certain period of time increases, so that more light is scattered and the amount of the transmitted light is reduced. Thus, the concentration of the antigen can be quantified from the amount of light measured as reaction process data.

Higher sensitivity of the latex immunoassay is desired in recent years and hence the measurement of scattered light rather than transmitted light has been attempted. For example, a system is disclosed that separates transmitted light and scattered light using a diaphragm and measures the absorbance and the scattered light at the same time (see PTL 3). The diameter and the like of reagent particles suitable for the measurement of scattered light are also disclosed (see PTL 4).

CITATION LIST

Patent Literatures

PTL 1: U.S. Pat. No. 4,451,433 A
PTL 2: U.S. Pat. No. 1,612,184
PTL 3: JP 2001-141654 A
PTL 4: U.S. Pat. No. 1,635,792

Non-Patent Literature

NPL 1: C. F. Bohren and D. R. Huffman, Absorption and Scattering of Light by Small Particles, J. Wiley & Sons, 1983.

SUMMARY OF INVENTION

Technical Problem

Although PTL 2 roughly discloses a wavelength, a particle diameter and the like for high sensitivity, they are directed to the measurement of the absorbance and it is unclear whether they can be applied to the measurement of scattered light. PTL 3 also discloses a configuration to achieve a high sensitivity by measuring transmitted light and scattered light at the same time, but the configuration is not considered as being suitable for an automated analyzer. In addition, suitable conditions including reagents are not considered.

Latex particles having a diameter (hereinafter referred to as a "particle diameter") of less than or equal to 500 nm are mainly used for a latex reagent, and the light scattering characteristics (scattered light intensity and its angular distribution) of individual particles are considered to vary greatly depending on the ratio of a particle diameter and a wavelength (see NPL 1). Thus, in the case of the measurement of scattered light, sensitivity can vary greatly depending on the selection of a particle diameter, a wavelength, and the like. The measurement of scattered light is described in PTL 4, but it is in the same scope as the measurement of the absorbance described in PTL 2, whereby, if used to measure the scattered light, it is understood that the measurement described in PTL 4 is not necessarily associated with a wavelength and a particle diameter suitable for uniformly high sensitivity, and it is concerned that the sensitivity is degraded depending on some wavelengths and particle diameters. However, an experiment by changing the wavelength, particle diameter, and the like requires significant time and cost, and a comprehensive trend is actually difficult to be understood.

Further, conditions in consideration of binding or the like of an antibody to sensitize a latex surface have not been studied. That is, the relationship between a wavelength and a light-receiving angle as device conditions and a particle diameter, density, a binding constant of antigen to antibody, and the like as reagent conditions when measuring scattered light on an automated analyzer and the sensitivity is not clear, and a suitable combination of conditions to perform the latex immunoassay with a high sensitivity is not known.

The present invention provides a device and conditions suitable for a reagent for performing latex immunoassay with a high sensitivity using a method of measuring scattered light on an automated analyzer.

Solution to Problem

The invention estimates the number of aggregates expected for a certain reaction time based on a binding constant in an antigen-antibody reaction and performs a simulation by optical modeling of the aggregates, thereby obtaining conditions for a reagent and a device under which changes of scattered light associated with the aggregation are likely to occur.

An automated analyzer of the invention includes a sample container that holds a sample, a reagent container that holds a reagent containing latex particles the average peak particle diameter of which ranges from 0.3 μm to 0.43 μm and to which antibodies are sensitized, a reaction container that holds a reaction solution into which the sample in the sample container and the reagent in the reagent container are mixed, a rotating mechanism that rotationally moves the reaction container, a light source unit that irradiates the reaction solution in the reaction container with irradiation light having a wavelength in the range of 0.65 to 0.75 μm, and a photodetector that is disposed at a light-receiving angle of 15° to 35° with respect to the irradiation direction of the irradiation light and receives scattered light generated from the reaction solution during the rotational movement of the reaction container. Here, the reaction solution contains the latex particles at a concentration at which the absorbance to irradiation light having a wavelength of 0.7 μm is 0.25 abs to 1.10 abs, and a change in the amount of scattered light caused by the aggregation of the latex particles through antigens in the sample is measured.

As to the concentration of latex particles contained in a reaction solution, the concentration at which the absorbance to irradiation light having a wavelength of 0.7 μm is 0.25 abs to 0.50 abs is more preferable, and the concentration at which the absorbance is 0.25 abs to 0.31 abs is still more preferable.

In addition, an analyzing method of the invention is the method analyzing a substance to be measured based on an antigen-antibody reaction using an automated analyzer, including: preparing a reaction solution by mixing, in a reaction container, a sample and a reagent containing latex particles the average peak particle diameter of which ranges from 0.3 μm to 0.43 μm and to which antibodies are sensitized; irradiating the reaction solution in the reaction container with irradiation light having a wavelength in the range of 0.65 to 0.75 μm during the rotational movement of the reaction container, and detecting scattered light at an angle of 15° to 35° with respect to the irradiation direction of the irradiation light; and measuring a change in the amount of scattered light caused by the aggregation of the latex particles through antigens in the sample, wherein the reaction solution contains the latex particles at a concentration at which the absorbance to irradiation light having a wavelength of 0.7 μm is 0.25 abs to 1.10 abs.

Advantageous Effects of Invention

The invention can measure the aggregation of latex particles using an antigen-antibody reaction with a high sensitivity and can measure down to the low concentration. Thus, the antigen or the antibody at low concentration can be calculated.

Problems, configurations, and advantageous effects other than those described above will become apparent from the following description of embodiments.

DESCRIPTION OF EMBODIMENTS

Embodiments of the invention will now be described with reference to the drawings. The following device configuration (wavelength of irradiation light and angle to receive scattered light), which is useful to a scattered light measuring unit incorporated in an automated analyzer, is selected.

First, the wavelength of the irradiation light is considered as follows. Since a scattered light measuring unit mounted on an automated analyzer is used at the same time as a conventional absorption photometer, the scattered light measuring unit is required to use a certain amount of a blood sample suitable for the absorption photometer, and may be affected by chyle, hemolysis, and jaundice as disturbance factors contained in the sample. The chyle, the hemolysis, and the jaundice cause a large absorption at wavelengths less than 650 nm. It means that the wavelength of the irradiation light is preferably 650 nm or more so as to be insulated from disturbance effects contained in the sample. In addition, the automated analyzer, which needs to measure during the rotational movement of a cell, is required to align the cell and an irradiation light flux with an accuracy of 1 mm or less by performing adjustment or the like during site maintenance so as not to produce stray light. In order to improve maintainability, the presence or absence of the stray light must be able to be confirmed visually. As such, the wavelength of the irradiation light is preferably in the range of 400 to 750 nm in the visible light region so as to be aligned easily. The wavelength range of 650 to 750 nm, which satisfies the conditions described above, is preferably selected.

A special-purpose machine dedicated to the measurement of scattered light, instead of an automated analyzer, does not rotate a cell during the measurement and requires no alignment accuracy between the cell and a light flux. Therefore fine adjustment is not required, and the wavelengths outside the visible light region can be used for measurement. However, using invisible light to measure the scattered light on the automated analyzer reduces maintainability and is not suitable for practical use.

The angle to receive scattered light is selected as follows. Since the measurement is performed on the automated analyzer, transparent light needs to be measured at the same time. As such, a square cell having a transparent surface through which transmitted light passes is used. The square cell has a structure suitable for the measurement of the transmitted light, and a measurement angle is limited when the scattered light is measured. Specifically, the transparent surface is designed to have a minimum optical distortion compared to other surfaces, and only light that passes through the transparent surface can be measured with high accuracy due to the cells located adjacent to each other. Accordingly, scattered light passing through the front surface or the rear surface of the cell needs to be measured. That is, the scattered light needs to be measured at the front or the rear with respect to the forward traveling direction of the irradiation light, where, since the amount of light needs to be ensured to reduce noise, receiving scattered light on the front side having a large amount of light compared with the rear side is generally advantageous, so that an angle of 35° or less is desired. In addition, an angle less than 15° sometimes increases noise under the influence of the transmitted light that is two orders of magnitude or more stronger than the scattered light. Thus, a scattered light-receiving angle of 15° to 30° in air is selected.

In view of the configuration of the device described above, a reagent composition useful for the measurement of the scattered light is also considered. First, the average particle diameter of the particles needs to be 0.25 μm or more in order to ensure a certain amount of the scattered light. The average particle diameter of the particles also needs to be 0.50 μm or less in order to maintain a reagent without precipitation for a long period of time. As such, the particle diameter range of latex particles is determined to be 0.25 to 0.50 μm.

In addition, the density of the latex particles in a reaction solution to ensure a certain amount of light needs to be 0.25 abs or more in terms of absorbance (at a wavelength of 0.7 μm). In view of the measurement range of the transmitted light, the density of the latex particles is also desired to be 1.5 abs or less in terms of absorbance before aggregation (at a wavelength of 0.7 μm). This is because, if more than that, the measurement of the transmitted light may deviate from the measurement range in terms of linearity and reproducibility.

Figure 1:
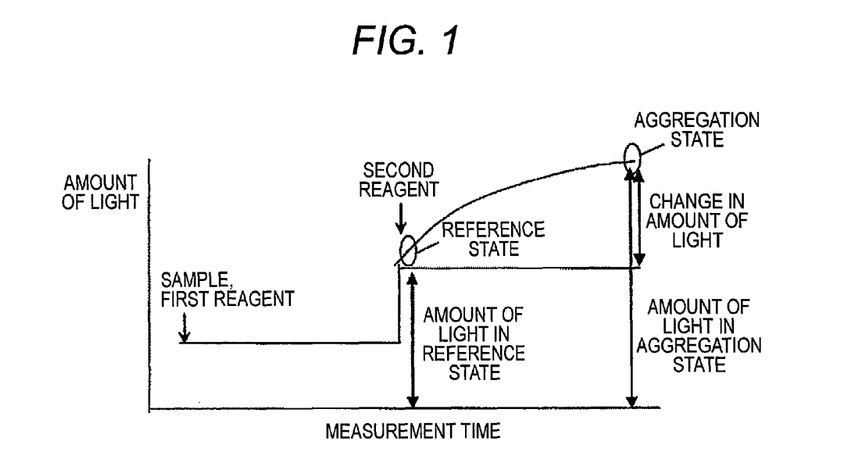
FIG. 1 is a schematic diagram for the measurement of scattered light.

An evaluation index for evaluation using these requirements is considered. FIG. 1 is a schematic diagram illustrating the time course of scattered light measurement using an antigen-antibody reaction. An automated analyzer having a scattered light measuring unit mixes a second reagent in which latex particles are dispersed with a sample to which a first reagent (reference state) is added, and detects a change in the amount of scattered light or transmitted light after a certain period of time passes (aggregation state). The automated analyzer is separately provided with calibration data obtained by measuring a change in the amount of light using known concentration of antigen and calculates the concentration of the antigen in the sample by comparing with the data, wherein, since the change in the amount of light is also proportional to the intensity of the irradiation light, the rate of change in the amount of light is defined by dividing the change in the amount of light by the amount of light in the reference state similarly proportional to the intensity of the irradiation light. A larger rate of change in the amount of light is capable of capturing a slighter change in aggregation. Additionally, the ratio of the rate of change in the amount of the scattered light to the rate of change in the amount of the transmitted light is defined as the ratio of the rate of change in the amount of light ("the rate of change in the amount of scattered light"/"the rate of change in the amount of transmitted light"). Since the larger ratio is contemplated to be more sensitive in the measurement of the scattered light, the following evaluation is performed by using the ratio of the rate of change in the amount of light as the evaluation index.

Then, to what extent latex particles in the reaction solution aggregate is assumed as follows. The concentration of a substance to be measured, which can be measured by conventional latex immunoassay, is contemplated to be in the range of about $10^{-11}$ mol/L or more. High sensitivity configuration that can measure antigen at a low concentration of about $10^{-12}$ mol/L is considered.

Here, if the density of the latex particles contained in the reaction solution is too thin, the amount of scattered light is reduced without most of irradiation light being scattered. This result in an increase in relative noise in signals received. Accordingly, latex particles at a concentration of about $10^6$ particles/mm$^3$ or higher are generally dispersed in the reaction solution in order to obtain a scattered light to some extent. The density of the latex particles is too large enough compared to an antigen concentration of $10^{-12}$ mol/L ($\approx 6 \times 10^5$ pieces/mm$^3$) as a detection target. That means a state in which a plurality of latex particles per molecule of antigen as a substance to be measured is dispersed. Thus, the aggregation rate of the latex particles that aggregate for a certain reaction time (the rate of the volume of aggregating latex particles of all the latex particles) is considered to be proportional to a binding rate as the rate of the antigens bound to the antibodies of all the antigens in the reaction solution.

In the following description, the number of antibodies in the reaction solution is estimated assuming that the number of antibodies sensitized to unit surface area of a particle is constant, and the binding rate of the antigens, that is, the aggregation rate of the particles, is evaluated.

Figure 2:
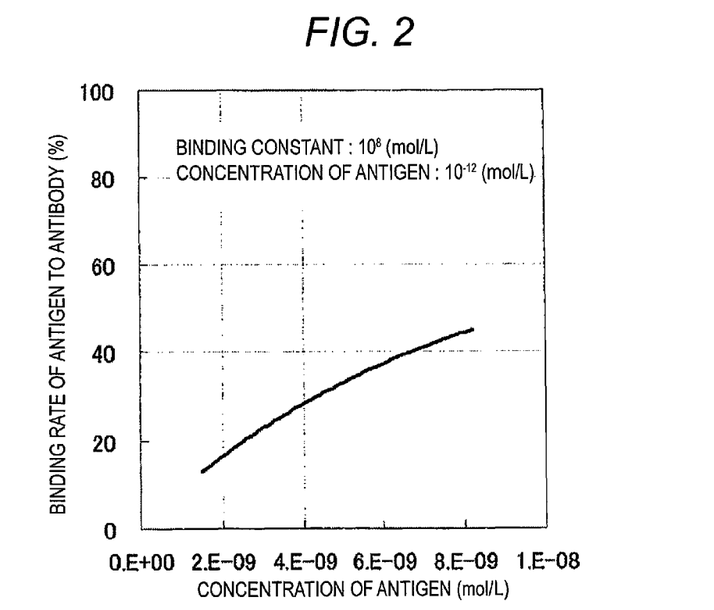
FIG. 2 is a diagram illustrating the antibody concentration dependence of the binding rate of antigens.

In the case of a reaction solution containing latex particles with the same particle diameter and with a different number density, the number of antibodies in the reaction solution is proportional to the number density of the latex particles. A density of the latex particles of 0.25 abs to 1.5 abs in terms of absorbance (at a wavelength of 0.7 μm) is equivalent to $2.8 \times 10^6$ to $1.7 \times 10^7$ pieces/mm$^3$ in terms of the number density of particles with a diameter of 0.3 μm. Assuming the diameter of an antibody is 15 nm and estimating that the ratio of sensitized active antibodies to maximal density where antibodies are laid all over the surface of the particle is 10%, antibody density on the particle surface is 510 pieces/μm$^2$. Additionally, assuming a single antibody has two reactive groups, about 290 binding sites of the antibodies on the surface of the particle with a diameter of 0.3 μm are present so that the concentration of the binding sites of the antibodies in the reaction solution is in the range of about $1.4 \times 10^{-9}$ to $8.2 \times 10^{-9}$ mol/L, whereby the concentration has a width of 6-fold. Here, as illustrated in FIG. 2, the binding rate of the antigen to the antibody is approximately proportional to the concentration of the antibody in the general range of binding constant of antigen-antibody reaction: $10^8$ mol/L, concentration of antigen: $10^{-12}$ mol/L, and concentration of antibody: $1.4 \times 10^{-9}$ to $8.2 \times 10^{-9}$ mol/L. That is, the aggregation rate of the latex particles, the binding rate of the antigen, and the concentration of the antibody are proportional to the binding rate of the antigen, the concentration of the antibody, and the number density of the latex particles, respectively, and as a result the aggregation rate of the latex particles is approximately proportional to the number density of the latex particles.

On the other hand, when the weight percent concentration of the reaction solution of latex particles is constant and the latex particles have different diameters, the number of particles is the reciprocal of the cube of the particle diameter. In addition, the surface area of the particles is proportional to the square of the particle diameter of each particle, and as a result the entire antibody concentration in the reaction solution is proportional to the reciprocal of the particle diameter. Therefore the antibody concentration range of the reaction solution in a particle diameter range width to be considered of 0.25 to 0.5 μm is less than or equal to 2-fold and is small compared to a density considering width (6-fold) of the particles described above so that the number of aggregating aggregates is assumed to be constant in the following optical simulation.

Figure 3:
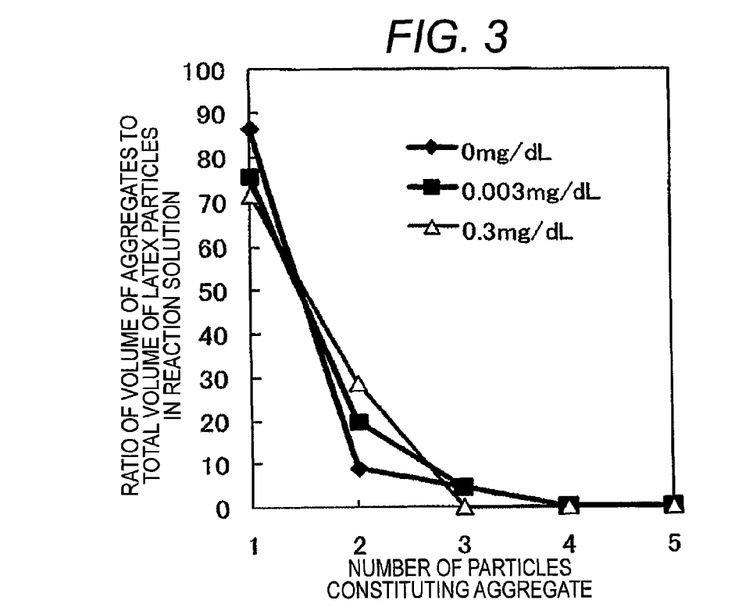
FIG. 3 is a diagram illustrating the antigen concentration dependence of the number of particles constituting an aggregate.

Moreover, at the thin enough concentration of the antigen, the aggregate is mainly considered to be made of two connected particles. FIG. 3 is a diagram illustrating an exemplary distribution of the number of latex particles in the aggregate per CRP antigen concentration (0 to 0.3 mg/dL (measurable range of reagent: 0.01 to 42 mg/dL)) of Nanopia CRP (manufactured by the SEKISUI MEDICAL CO., LTD). A calibrator (2.4 μL) at each CRP concentration, the first reagent (120 μL), and the second reagent (120 μL) are mixed, and the reaction solution is applied to a substrate after 300 seconds of mixing, thereby forming a sample. The distribution is determined by observing the sample with a scanning electron microscope and by counting the number of latex particles making up the aggregate, whereby it is actually confirmed that the aggregates made of two latex particles among aggregates increases with the increasing concentration of antigen.

Based on the above, the rate of the volume of two particle-aggregates per particle diameter and density of the latex particles at the same concentration of antigen is set.

Mishchenko M I, Travis L D, Mackowski D W., T-matrix computations of light scattering by nonspherical particles: a review. J Quant Spectrosc Radiat Transfer, 1996, confirms by the electric field calculation that a spheroid of approximately the same type as the two particle-aggregate is approximately equal to a true sphere particle equal to its cross-sectional area with respect to scattering cross-section and intensity distribution of each angle of scattered light. In reference to this, optical modeling is performed by replacing the respective two particle-aggregate with true sphere particle having a cross-sectional area equal to the sum of the cross-sectional area of respective carrier particles of the two particle-aggregate.

Wavelength: 700 nm, angle: 20° (±2.5°), binding constant of antigen to antibody: $10^8$ mol/L or more, diameter range of reagent particle: 0.25 to 0.50 μm, and density: absorbance before aggregation 0.25 to 1.5 abs are used as parameters in view of the range assumed in measuring the scattered light on the automated analyzer as described above, and the amounts of the scattered light from the reaction solution in the reference state and the aggregation state are calculated by an optical simulation using the Monte Carlo method. The scattered light theory described in NPL 1 is used for the optical simulation.

Figure 4:
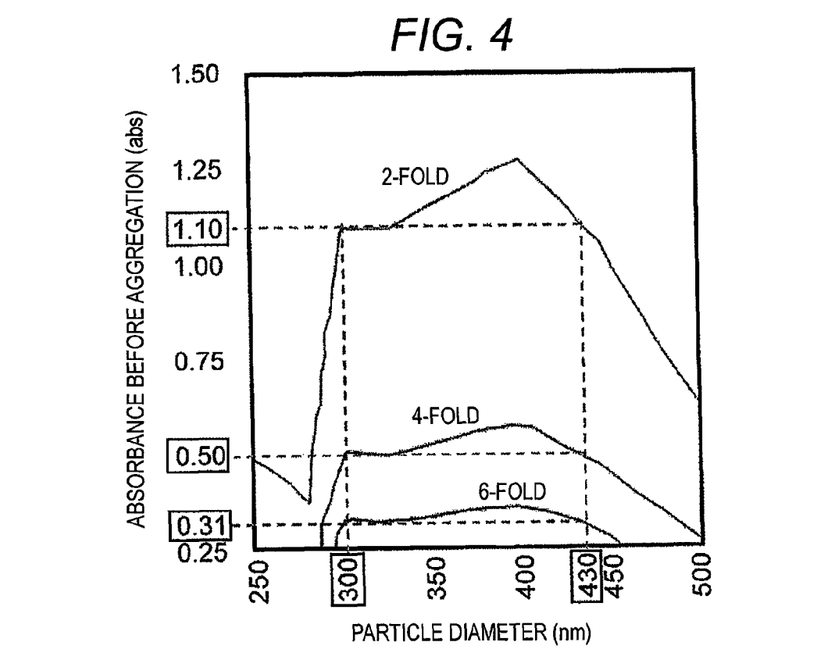
FIG. 4 is a diagram illustrating the rate of change in the amount of scattered light (the ratio of the rate of change in the amount of light) with respect to the rate of change in the amount of transmitted light.

From the results obtained by the optical simulation, FIG. 4 illustrates the ratio of the rate of change in the amount of light that is obtained by dividing the rate of change in the amount of scattered light caused by the aggregation of the latex particles by the rate of change in the amount of transmitted light. Since a larger rate of change in the amount of light is capable of capturing a slighter change in aggregation, a particle diameter and density with a greater ratio of the rate of change in the amount of light can be considered to be more sensitive in measuring scattered light rather than in measuring transmitted light in FIG. 4. Thus, the following conditions are found that are determined to be suitable for the measurement of the scattered light on the automated analyzer. Note that the binding constant of the antigen to the antibody and the concentration of the antigen used as parameters in the simulation described above are common values and does not affect the ratio of the rate of change in the amount of light illustrated in FIG. 4 because the above assumption of the optical simulation does not change even if they change to a certain extent. The relationship illustrated in FIG. 4 is satisfied even if the binding constant of the antigen to the antibody is more than or equal to $10^8$ mol/L and is less than or equal to $10^{11}$ mol/L, for example.

From FIG. 4, it is found that the measurement of the scattered light achieves a high sensitivity more than or equal to 2-fold the measurement of the transmitted light, provided that a diameter of the latex particles in the reagent is 0.3 μm to 0.43 μm and a density before aggregation of latex particles in the reaction solution is 0.25 to 1.10 abs in terms of absorbance. Further, it is found that the measurement of the scattered light achieves a high sensitivity more than or equal to 4-fold the measurement of the transmitted light, provided that a diameter of the latex particles in the reagent is 0.3 μm to 0.43 μm and a density before aggregation of latex particles in the reaction solution is 0.25 to 0.50 abs in terms of absorbance. Still further, it is found that the measurement of the scattered light achieves a high sensitivity more than or equal to 6-fold the measurement of the transmitted light, provided that a diameter of the latex particles in the reagent is 0.3 μm to 0.43 μm and a density before aggregation of latex particles in the reaction solution is 0.25 to 0.31 abs in terms of absorbance.

The device configuration and the reagent composition described above enables the measurement of the scattered light with a high sensitivity when the change in the amount of light associated with the latex particle aggregation reaction is measured.

Figure 5:
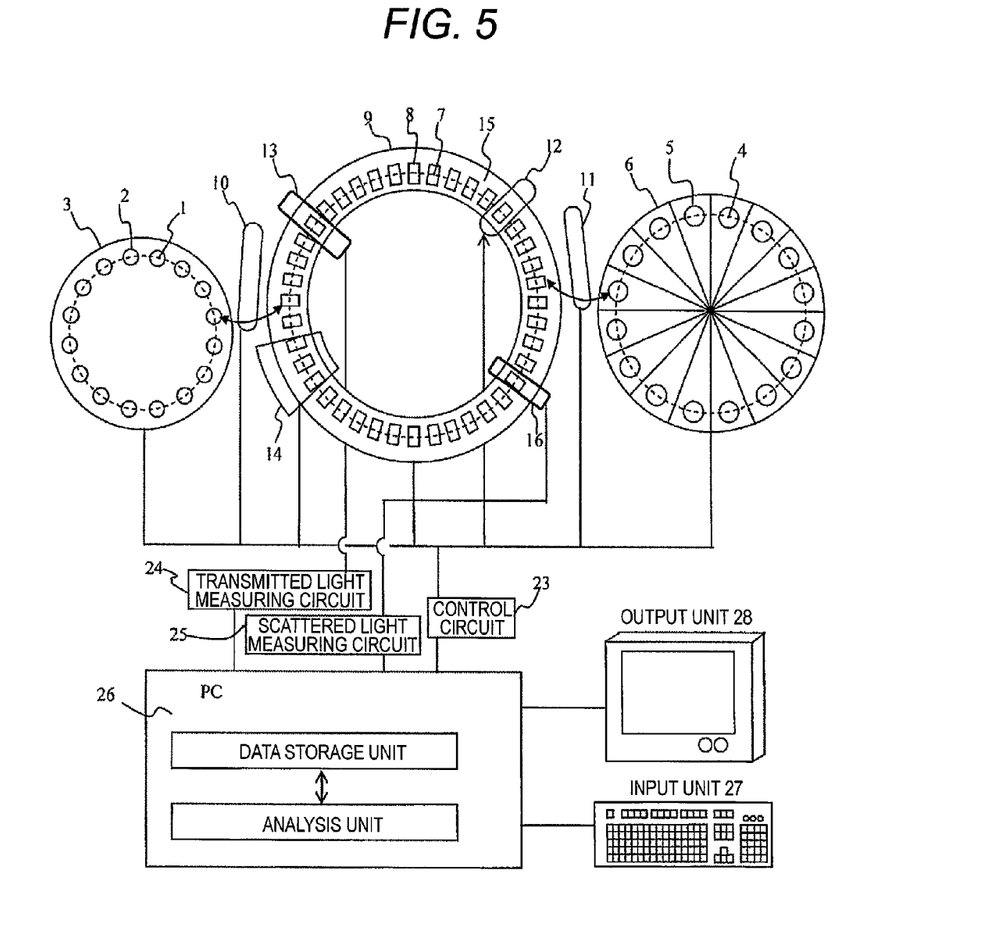
FIG. 5 is a schematic diagram illustrating an example of the overall configuration of an automated analyzer.

FIG. 5 is a schematic diagram illustrating an example of the overall configuration of an automated analyzer according to the invention. An automated analyzer of the present embodiment can measure transmitted light and scattered light at the same time. The automated analyzer of the present embodiment includes three types of discs, that is, a sample disc 3, a reagent disc 6, and a cell disc 9, a dispensing mechanism that moves a sample and a reagent between these discs, a control circuit 23 for controlling them, a transmitted light measuring circuit 24, a scattered light measuring circuit 25, a data processing unit 26 such as a PC (computer) for processing data measured, and an input unit 27 and an output unit 28 as an interface to input and output data from and to the data processing unit 26. The data processing unit 26 includes an analysis unit for analyzing the data and a data storage unit for storing control data, measurement data, data used for analysis, analysis result data, and the like.

The circumference of the sample disc 3 is provided with a plurality of sample cups 2 holding a sample 1. The reagent disc 6 is provided with a plurality of reagent bottles 5 containing a reagent 4. The circumference of the cell disc 9 is provided with a plurality of cells 8 in which a reaction solution 7 is prepared by mixing the sample 1 and the reagent 4. A sample dispensing mechanism 10 transfers a predetermined amount of the sample 1 from the sample cup 2 to the cell 8. A reagent dispensing mechanism 11 transfers a predetermined amount of the reagent 4 from the reagent bottle 5 to the cell 8. A stirring unit 12 stirs and mixes the sample 1 and the reagent 4 in the cell 8. A cleaning unit 14 discharges the reaction solution 7 from the cell 8 where an analysis is completed and makes it clean. A next sample 1 is dispensed into the cell 8 cleaned from the sample dispensing mechanism 10 again, a new reagent 4 is dispensed from the reagent dispensing mechanism 11, and they are used for another reaction. The cell 8 is immersed in a constant temperature fluid 15 in a thermostatic chamber in which temperature and flow rate are controlled, and the cell 8 and the reaction solution 7 therein are transferred with temperature kept constant. For example, water is used for the constant temperature fluid 15, and the temperature of the constant temperature fluid is controlled at 37° C.±0.1° C. by a control circuit. The part of the circumference of the cell disc is provided with a transmitted light measuring unit 13 and a scattered light measuring unit 16.

The transmitted light measuring unit 13 may be configured, for example, such that the cell 8 is irradiated with light from a halogen lamp light source, and then transmitted light is dispersed by a diffraction grating and is received by a photodiode array. The wavelengths to be received are 340 nm, 405 nm, 450 nm, 480 nm, 505 nm, 546 nm, 570 nm, 600 nm, 660 nm, 700 nm, 750 nm, and 800 nm, for example. The amount of the transmitted light received by the photodiode array is transmitted to the data storage unit of the PC through the transmitted light measuring circuit 24.

Figure 6:
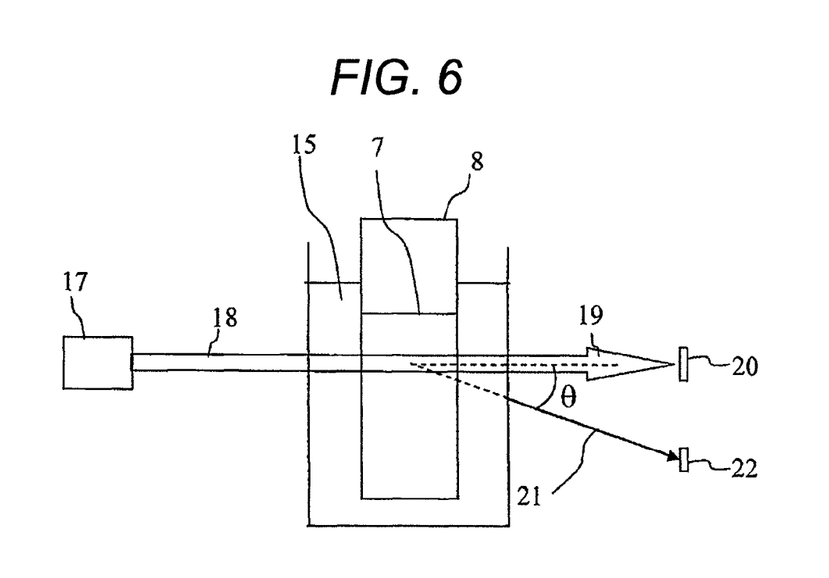
FIG. 6 is a schematic diagram of a scattered light measuring unit.

FIG. 6 is a schematic diagram of the scattered light measuring unit 16. An LED light source, for example, may be used as a light source. The cell 8 being moved is irradiated with an irradiation light 18 from an LED light source unit 17, and a transmitted light 19 is received by a transmitted light receiver 20 and a scattered light is received by a scattered light receiver 22. The LED light source unit 17 may use a wavelength of 700 nm, for example, for the irradiation light. While the embodiment uses an LED as the light source, a laser, a xenon lamp, or a halogen lamp may also be used. The scattered light receiver 22 measures the scattered light 21 in a direction tilted by an angle θ in air with respect to an optical axis. The angle θ can be any angle in the range of 15° to 35°, and the embodiment employs an angle θ of 20°. The scattered light receiver 22 is disposed in a generally vertical plane with respect to the moving direction of the cell 8 when the cell disc 9 is rotated. Here, the reference position of the angle θ starts from the center of the length through which the light passes in the cell 8. Receivers that receive light with different scattering angles are provided as a means that receives scattered light from the reaction solution 7, and some of the receivers can obtain a signal.

While photodiodes are disposed at respective angles as the light receivers 20 and 22 in the embodiment, a single linear array having multiple light receivers therein may be configured to receive multi-angled scattered light. This can widen the choice of light-receiving angles. Instead of the light receiver, an optical system such as a fiber and a lens, which is disposed at a position to receive the scattered light, can guide the light to a scattered light receiver disposed at another position.

The quantification of the concentration of a substance to be measured in a sample 1 is performed in the following procedure. First, the sample dispensing mechanism 10 dispenses a predetermined amount of the sample 1 contained in the sample cup 2 into the cell 8. Then, the reagent dispensing mechanism 11 dispenses a predetermined amount of the reagent 4 contained in the reagent bottle 5 into the cell 8. When they are dispensed, the sample disc 3, the reagent disc 6, and the cell disc 9 are rotated by respective drive units under the control of the control circuit 23, and the sample cup 2, the reagent bottle 5, and the cell 8 are moved, timed to dispensing by the dispensing mechanisms 10 and 11. Next, the stirring unit 12 stirs the sample 1 and the reagent dispensed into the cell 8 to prepare the reagent solution 7. Transmitted light and scattered light from the reagent solution 7 are measured each time they pass through the measurement positions of the transmitted light measuring unit 13 and the scattered light measuring unit 16 during rotation of the cell disc 9, which are stored sequentially as reaction process data in the data storage unit of the data processing unit 26 from the transmitted light measuring circuit 24 and the scattered light measuring circuit 25. After measurement for a certain period of time, for example, 10 minutes, the cell 8 is cleaned by the cleaning unit 14, and an analysis for the next test item is performed. Meanwhile, if necessary, other reagents 4 are additionally dispensed into the cell 8 by the reagent dispensing mechanism 11, are stirred by the stirring unit 12, and are further measured for a certain period of time. Thus, the reaction process data of the reaction solution 7 at a predetermined time interval is stored in the data storage unit. The analysis unit determines a change in the amount of light due to reaction for a certain period of time from the stored reaction process data at a single light-receiving angle or a plurality of light-receiving angles of the scattered light measuring unit, and quantitative results are calculated based on calibration curve data stored in the data storage unit in advance and are displayed by the output unit. Data necessary for control and analysis of each unit is input from the input unit 27 to the data storage unit of the data processing unit 26. Data and results stored in storage units and an alarm are output on a display or the like by the output unit 28.

Figure 7:
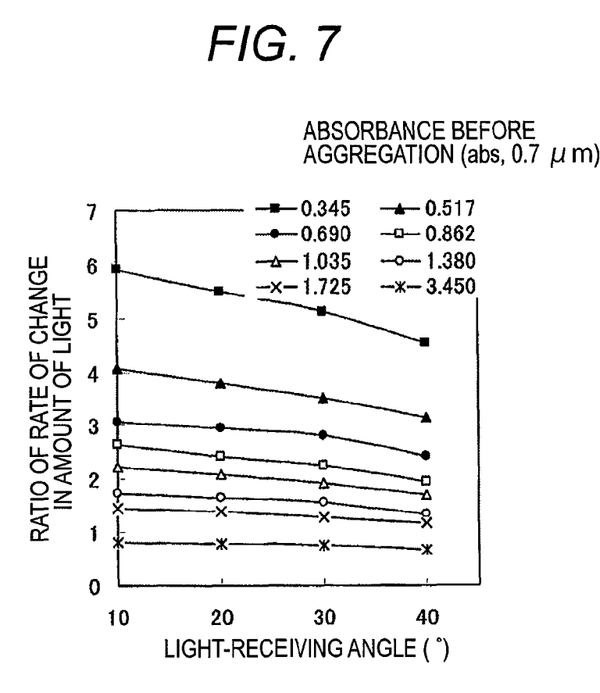
FIG. 7 is a diagram illustrating the angular dependence of the ratio of the rate of change in the amount of light.

Wavelengths for the measurement of scattered light are only necessary to be in the range of 650 nm to 750 nm. A scattered light-receiving angle of 15° to 35° is allowable. FIG. 7 illustrates the ratio of the rate of change in the amount of light for each particle diameter and particle density (as indicated by absorbance at a wavelength of 700 nm) calculated by the optical simulation described above where, in the case of forward scattering (15° to 30°), the ratio of the rate of change in the amount of light is confirmed to be almost unchanged.

The particle diameter of latex particles contained in the reaction solution 7 ranges from 0.3 μm to 0.43 μm. The rate of change in the amount of light greater than that of the transmitted light can be obtained, as illustrated in FIG. 4, using the latex particles in this particle diameter range, and this allows the antigen at a smaller concentration than ever before to be measured.

Since the thinner the concentration of the latex solution contained in the reaction solution 7 is, irradiation light is less likely to be scattered by the reaction solution 7, achieving a density of the latex particles contained in the reaction solution 7 of 0.25 abs or more in terms of absorbance can sufficiently increase the amount of the scattered light measured by the scattered light receiver 22.

Antibodies sensitized to the carrier as well as latex particles used in the antigen-antibody reaction make up most of the reagent cost. As such, achieving a density of the latex particles contained in the reaction solution 7 of 0.25 abs to 1.10 abs in terms of absorbance can reduce latex particles used and antigens sensitized to the carrier while increasing the ratio of the rate of change in the amount of light, thereby reducing the manufacturing cost of the reagent.

Antibodies with a small binding constant are present in the antigen-antibody reaction. In order to obtain a higher ratio of the rate of change in the amount of light even in using the antibodies with such a small binding constant, the density of the latex particles contained in the reaction solution 7 can be achieved in the range of 0.25 abs to 0.5 abs in terms of absorbance.

Latex particles contained in the reaction solution 7 may be used the full width at half maximum of which particle diameter is within ±15% of the particle diameter at the peak of the distribution (peak particle diameter) in a particle diameter distribution based on the volume and the peak particle diameter of which particles is in the range of 0.3 μm to 0.43 μm. The diameters of small particles generally have a distribution, and the cost will be higher as the width of the distribution is reduced. Since FIG. 4 illustrates that the ratio of the rate of change in the amount of light is almost unchanged due to a difference in the particle diameter of a few percent, the use of latex particles the full width at half maximum of which particle diameter is within ±15% of the particle diameter at the peak of the distribution (peak particle diameter) in a particle diameter distribution based on the volume and the peak particle diameter of which particles is in the range of 0.3 μm to 0.43 μm can obtain a high ratio of the rate of change in the amount of light and reduce the cost. Alternatively, in order to reduce variations in scattered light intensity from the reaction solution due to variations in particle diameter, the full width at half maximum of the particle diameter may be within ±10% of the peak particle diameter. In order to reduce variation between the measurements of the same samples, the full width at half maximum of the particle diameter also may be within ±7% of the peak particle diameter.

The invention is not limited to embodiments described above, and may include various modifications. For example, the embodiments above are described in detail to clearly explain the invention and are not necessarily limited to those having all the configurations described. Part of the configuration of one embodiment can be replaced with the configuration of another embodiment, and the configuration of another embodiment can be also added to the configuration of one embodiment. Further, addition, deletion, and substitution of other configurations can be made for part of the configuration of the embodiments. Still further, the figures illustrate what is believed to be necessary for description, and they do not necessarily indicate all of configuration units and functions.

REFERENCE SIGNS LIST 1 sample
2 sample cup
3 sample disc
4 reagent
5 reagent bottle
6 reagent disc
7 reaction resolution
8 cell
9 cell disc
10 sample dispensing mechanism
11 reagent dispensing mechanism
12 stirring unit
13 transmitted light measuring unit
14 cleaning unit
15 constant temperature fluid
16 scattered light measuring unit
17 LED light source unit
18 irradiation light
19 transmitted light
20 transmitted light receiver
21 scattered light
22 scattered light receiver
23 control circuit
24 transmitted light measuring circuit
25 scattered light measuring circuit
26 data processing unit
27 input unit
28 output unit

The invention claimed is:

1. An automated analyzer, comprising:
a sample container that holds a sample;
a reagent container that holds a reagent containing latex particles having an average peak particle diameter ranging from 0.3 pm to 0.43 pm and to which antibodies are sensitized;
a reaction container that holds a reaction solution into which the sample in the sample container and the reagent in the reagent container are mixed;
a rotating mechanism that rotationally moves the reaction container;
a light source that irradiates the reaction solution in the reaction container with irradiation light having a wavelength in the range of 0.65 to 0.75 pm;
a photodetector that is disposed at a light-receiving angle of 150 to 350 with respect to the irradiation direction of the irradiation light and is configured to detect scattered light generated from the reaction solution upon irradiation by the light source; and
a computer, having a processor and a memory, coupled to the rotating mechanism, light source, and photodetector, the memory storing instructions that when executed by the processor cause the processor to:
instruct the rotating mechanism to rotate the reaction container,
instruct the photodetector to detect scattered light generated from the reaction solution at a first time and store first detected scattered light data from the photodetector in the memory,
instruct the photodetector to detect scattered light generated from the reaction solution at a second time, which is a predetermined amount of time after the first time, and store second scattered light data from the photodetector in the memory,
calculate a change in an amount of scattered light data based on the first detected scattered light data and the second detected scattered light data, and
determine a concentration of antigen or antibody in the reaction solution in the range of $10^{-11}$ mol/L to $10^{-12}$ mol/L based on the calculated change in the amount of scattered light,
wherein the reaction solution contains the latex particles at a concentration at which the absorbance to irradiation light having a wavelength of 0.7 pm is 0.25 abs to 1.10 abs.

2. The automated analyzer according to claim 1, wherein the latex particles are latex particles to which antibodies having a binding constant with the antigens contained in the sample that is more than or equal to $10^8$ mol/L and less than or equal to $10^{11}$ mol/L are sensitized.

3. The automated analyzer according to claim 1, wherein the reaction solution contains the latex particles at a concentration at which the absorbance to irradiation light having a wavelength of 0.7 μm is 0.25 abs to 0.50 abs.

4. The automated analyzer according to claim 1, wherein the reaction solution contains the latex particles at a concentration at which the absorbance to irradiation light having a wavelength of 0.7 µm is 0.25 abs to 0.31 abs.

5. The automated analyzer according to claim 1, wherein the full width at half maximum of the particle diameter of latex particles contained in the reagent is within ±15% of a peak particle diameter at the peak of the distribution in a particle diameter distribution based on the volume, and the peak particle diameter is in the range of 0.3 µm to 0.43 µm.

6. The automated analyzer according to claim 1, wherein the full width at half maximum of the particle diameter of latex particles contained in the reagent is within ±10% of a peak particle diameter at the peak of the distribution in a particle diameter distribution based on the volume, and the peak particle diameter is in the range of 0.3 µm to 0.43 µm.

7. The automated analyzer according to claim 1, wherein the full width at half maximum of the particle diameter of latex particles contained in the reagent is within ±7% of a peak particle diameter at the peak of the distribution in a particle diameter distribution based on the volume, and the peak particle diameter is in the range of 0.3 µm to 0.43 µm.

8. A method of analyzing a substance to be measured based on an antigen-antibody reaction using an automated analyzer, comprising:

preparing a reaction solution by mixing, in a reaction container, a sample and a reagent containing latex particles the average peak particle diameter of which ranges from 0.3 µm to 0.43 µm and to which antibodies are sensitized;

irradiating the reaction solution in the reaction container with irradiation light having a wavelength in the range of 0.65 to 0.75 µm during rotational movement of the reaction container;

detecting scattered light, at an angle of 15° to 35° with respect to the irradiation direction of the irradiation light, generated from the reaction solution upon irradiation with the irradiation light at a first time;

detecting scattered light, at an angle of 15° to 35° with respect to the irradiation direction of the irradiation light, generated from the reaction solution upon irradiation with the irradiation light at a second time which is a predetermined amount of time after the first time;

measuring a change in the amount of scattered light based on the detected scattered light at the first time and the second time; and determining a concentration of antigen or antibody in the reaction solution in the range of $10^{-11}$ mol/L to $10^{-12}$ mol/L based on the calculated change in the amount of scattered light, wherein the reaction solution contains the latex particles at a concentration at which the absorbance to irradiation light having a wavelength of 0.7 µm is 0.25 abs to 1.10 abs.

* * * * *